(12) United States Patent
Robran

(10) Patent No.: US 12,109,140 B2
(45) Date of Patent: Oct. 8, 2024

(54) ORTHOPEDIC DEVICE FOR STABILIZING THE LOWER LEG AND ENABLING KNEE MOTION THERAPY

(71) Applicant: BONE FOAM, INC., Corcoran, MN (US)

(72) Inventor: Chad L. Robran, Plymouth, MN (US)

(73) Assignee: Bone Foam, Inc., Corcoran, MN (US)

( * ) Notice: Subject to any disclaimer, the term of this patent is extended or adjusted under 35 U.S.C. 154(b) by 298 days.

(21) Appl. No.: 17/022,824

(22) Filed: Sep. 16, 2020

(65) Prior Publication Data

US 2021/0077287 A1 Mar. 18, 2021

Related U.S. Application Data

(60) Provisional application No. 63/078,565, filed on Sep. 15, 2020, provisional application No. 62/901,783, filed on Sep. 17, 2019.

(51) Int. Cl.
| | | |
|---|---|---|
| *A61F 5/00* | (2006.01) | |
| *A61F 5/01* | (2006.01) | |
| *A61F 5/37* | (2006.01) | |

(52) U.S. Cl.
CPC .......... *A61F 5/0116* (2013.01); *A61F 5/3761* (2013.01)

(58) Field of Classification Search
CPC .. A61F 5/042; A61F 5/05; A61F 5/058; A61F 5/05841; A61F 5/0585; A61F 5/37;
(Continued)

(56) References Cited

U.S. PATENT DOCUMENTS 2,478,497 A * 8/1949 Morrison .............. A61F 13/069
 5/651
3,511,233 A 5/1970 Elbert, Jr.
(Continued)

FOREIGN PATENT DOCUMENTS

WO 2019173537 A1 9/2019

OTHER PUBLICATIONS

International Search Report and Written Opinion received for PCT Patent Application No. PCT/US2020/051263, mailed on Nov. 24, 2020, 11 pages.

(Continued)

*Primary Examiner* — Adam Baker
(74) *Attorney, Agent, or Firm* — Workman Nydegger

(57) ABSTRACT

A support device provides elevation and support for a patient's foot and limits lateral and medial rotation of the foot relative to the knee. This protects the knee from injury during healing. The device includes a generally flat main body, two spaced-apart lateral ridges, and a medial depression between the lateral ridges that provides a support surface on which the foot may be positioned. The lateral ridges can extend to a height above the support surface so that inner side surfaces of the lateral ridges are adjacent to a majority of a foot placed in the medial depression. The support surface can include a heel aperture extending through the main body to provide a continuous heel pocket allowing the heel to remain freely suspended when the foot is placed in the device. The device can additionally or alternatively include a slidable base allowing the device to better slide on a surface enabling the user to perform therapeutic exercises.

21 Claims, 10 Drawing Sheets

(58) Field of Classification Search
CPC .... A61F 5/3761; A61F 5/3769; A61F 5/0116; A61G 13/12; A61G 13/1205; A61G 13/123; A61G 13/1245; A61G 13/125; A61G 13/128; A61G 13/1285; A61G 13/1295; A61G 7/065; A61G 7/075; A61G 7/0755; A47C 16/02
USPC ........................................................ 128/882
See application file for complete search history.

(56) References Cited

U.S. PATENT DOCUMENTS

| | | | | |
|---|---|---|---|---|
| 4,409,975 A | * | 10/1983 | Simhoni | A61F 13/069 128/892 |
| 5,046,487 A | | 9/1991 | Scott | |
| 5,449,339 A | * | 9/1995 | Drennan | A61F 5/0195 128/882 |
| 5,584,303 A | | 12/1996 | Walle | |
| 5,603,336 A | * | 2/1997 | Shepich | A61F 5/3761 128/882 |
| 5,957,874 A | * | 9/1999 | Klein | A61F 5/0195 128/882 |
| 5,997,491 A | * | 12/1999 | Harris | A47C 20/021 128/882 |
| 8,176,585 B1 | * | 5/2012 | Isham | A61G 13/123 5/710 |
| 11,154,447 B2 | * | 10/2021 | Lucey | A61G 7/0755 |
| 2003/0159699 A1 | | 8/2003 | Anderson et al. | |
| 2005/0045265 A1 | * | 3/2005 | Pannell | B44C 1/105 427/282 |
| 2006/0053556 A1 | * | 3/2006 | Piontek | A61F 5/3707 5/622 |
| 2013/0012854 A1 | * | 1/2013 | Wens | A61F 5/0585 602/23 |
| 2013/0319426 A1 | * | 12/2013 | Castle | A61G 7/0755 128/845 |
| 2015/0150744 A1 | * | 6/2015 | Ware | A61G 13/1245 128/845 |
| 2018/0008499 A1 | | 1/2018 | Lucey et al. | |

OTHER PUBLICATIONS

International Preliminary Report on Patentability received for PCT Patent Application No. PCT/US2020/051263, mailed on Mar. 31, 2022, 8 pages.

European Search Report received for EP Patent Application No. 20864582.0, mailed on Sep. 20, 2023, 6 pages.

* cited by examiner

ORTHOPEDIC DEVICE FOR STABILIZING THE LOWER LEG AND ENABLING KNEE MOTION THERAPY

CROSS REFERENCE TO RELATED APPLICATION

This application claims the benefit of U.S. Prov App No. 62/901,783, filed Sep. 17, 2019, and U.S. Prov App No. 63/078,565, filed Sep. 15, 2020, which are incorporated by reference.

BACKGROUND

Following injury or a lower limb surgical procedure, especially knee surgery (such as total knee replacement, arthroscopic knee surgery, or ACL surgery), a patient often lies or is placed in a supine position, i.e. with the front (anterior) portion of the lower limb facing up and the back portion of the lower limb (posterior) facing downward. As part of the recovery, it is often required that the lower limb remain in a certain position, being isolated, immobilized, and elevated, for a prescribed time period.

Many kinds of undesirable movements are possible, however, during this time period of recovery. For example, natural movement may arise as the patient's foot naturally tends to rotate outwardly (laterally) or inwardly (medially) from the supine position. This lateral or medial foot rotation can exert undesirable torsion on an injured or newly repaired knee, potentially slowing recovery and possibly necessitating more surgery to fix any damage. Other undesirable movements may also need restraint.

In the context of medical recovery of extremity trauma, efforts may be taken to ensure that a patient's body is properly elevated, isolated, stabilized, and/or otherwise supported. The patient may lie, for example, in a supine position, with the ankle required to be isolated, elevated, immobilized, and supported. Furthermore, the natural inclination of the foot to rotate outwardly (laterally) or inwardly (medially) due to relaxation or gravity may in turn cause the tibia and fibula to rotate laterally or medially relative to the femur. This in turn may cause unwanted and potentially dangerous torsion or torque to the knee joint. For example, a patient recovering from knee surgery may incur serious pain, reinjure the knee, and even require additional surgery if the knee is not properly protected from torsion.

In some cases, physical rehabilitative therapy may be required following such an injury and/or surgery. Long-term therapeutic care is necessary to ensure proper healing and restoration of full range of motion, joint function, and muscle strength near the joint. Knee motion exercises may sometimes be recommended to help the patient restore normal movement in the joint and regain the strength to walk without assistance or limp and to get up and down from a chair or bed. A rehabilitation program may incorporate hip abduction and adduction exercises, and/or knee flexion and extension exercises, for example.

Proper positioning for recovery and rehabilitation requires a device which can properly position and isolate a limb. Additionally, devices used to isolate a limb for an extended period of time can cause discomfort to the patient and cause skin irritation and bed sores. As such, there remains a need for devices which can aid in recovery of a knee joint following injury and/or surgery. Such a device would ideally be capable of providing stabilization and support to the lower limb while providing adequate ventilation and optionally enabling and enhancing the ability to conduct rehabilitative therapy on the knee.

BRIEF SUMMARY

Disclosed herein are orthopedic devices configured for supporting and restraining rotation of the foot of a patient recovering from surgery, such as knee surgery. The devices help maintain knee extension and unwanted torsion on the knee joint by restraining foot rotation. Continuous extension of a surgically repaired knee and protection against unwanted torsion of the knee following surgery promote proper healing.

In some embodiments, orthopedic devices can be configured to elevate the foot and ankle to a level that lifts the knee above the surface on which the patient lies (e.g., floor, table, bed, couch, or other surface) so that the posterior side of the knee remains unsupported. This allows gravity to pull down on the posterior side of the knee, stretching and maintaining proper extension of the knee. Also, elevating the ankle and lower leg above the surface may be desirable to ensure proper blood flow for reduction of edema and promotion of healing.

Devices disclosed herein are configured to limit unwanted motion of the foot to stabilize and protect a recovering knee. For example, when the patient is lying in a supine position, the foot tends to rotate outwardly (laterally) or inwardly (medially) due to relaxation or gravity, which can cause the tibia and fibula to rotate laterally or medially relative to the femur. Such rotation may cause unwanted and potentially dangerous torsion or torque to a recovering knee joint. For example, a patient recovering from knee surgery may incur serious pain, reinjure the knee, and may require additional surgery if the knee is not properly protected from such torsion. The disclosed orthopedic devices are configured to cradle and support the foot, including the ankle and heel, in a manner that prevents, minimizes or reduces such rotation and allows the knee to be substantially free of torsional moments.

Support devices as disclosed herein may be used to isolate, elevate, immobilize, and support an ankle to provide restraint against foot and lower leg rotation. The patient may lie, for example, in a supine position with the foot, including ankle and heel, resting on or in a cavity of continuous or varying depth formed in the support device. The support device may include a main body with a generally flat lower surface, which can be sufficiently wide to prevent or limit rotation of the support device in response to foot rotation forces. The support device includes two spaced-apart lateral ridges extending upwardly along or near lateral edges of the main body and a medial depression between the lateral ridges that provides a support surface and cavity of continuous or varying depth in which the patient's foot may be positioned. The lateral ridges can be sufficiently tall relative to the foot to restrain the foot from medial and lateral rotations. The lateral ridges can be spaced apart to permit a foot to be placed into or lifted out of the medial depression without having to manipulate the support device (i.e., without having to spread apart the lateral ridges when inserting a foot into or removing the foot from the medial cavity). This ease of insertion and removal helps prevent injury to the patient's knee.

The support device may further comprise a medial ridge connected to and extending transversely between the lateral ridges to limit plantarflexion of the foot during recovery. The support device can terminate at a location proximal to the ankle and distal to the calf muscle so that the calf muscle and region behind the knee are not in contact with the support device and, in some embodiments, are not in contact with the surface on which the patient lies. This assists in maintaining the knee in an extended position.

The medial depression may further comprise a heel aperture extending from the medial depression all the way through the main body. The heel aperture may have a continuous diameter or varying diameter and may extend at an angle from an opening in the medial depression. The heel aperture accommodates differently sized heels and reduces or eliminates underlying pressure on the heel to prevent formation of long-term heel sores. In this way, the heel itself does not bear the weight of the patient's leg, which can instead be borne by one or more of the ankle, Achilles tendon, or lower leg below the calf muscle. The heel aperture can provide the additional benefits of ventilating the heel and ankle, permitting sluffed-off skin to fall away from the foot to prevent infections and bad odors, and promote firm placement of the foot within the support device to immobilize the knee.

In some embodiments, a device can be optionally configured to facilitate therapeutic exercises by the patient while the lower limb is supported by the device. In such embodiments, the therapeutic device may include a base with a low-friction bottom surface that permits the patient to move his/her leg while sliding the entire support device relative to the floor or other support surface. For example, with the device supporting the patient's foot, the patient may selectively flex and extend the knee and/or may selectively abduct and adduct the hip. The low-friction bottom surface of the base allows the device to slide along the floor or other surface so that the patient can readily perform motion exercises while the foot remains supported, properly aligned, and immobilized by the device in a non-rotating position relative to the knee.

The embodiments disclosed herein beneficially aid in maximizing range of motion, avoiding long-term adverse effects, speeding recovery times, reducing soreness, reducing immobility, reducing pain, and reducing the need for and/or amount of pain medication.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

DETAILED DESCRIPTION

Disclosed herein are orthopedic devices configured for supporting and restraining rotation of the foot of a patient recovering from surgery, such as knee surgery. The devices help maintain knee extension and unwanted torsion on the knee joint by restraining foot rotation. Continuous extension of a surgically repaired knee and protection against unwanted torsion of the knee following surgery promote proper healing. Some embodiments are designed to also limit plantarflexion of the foot. An orthopedic device can optionally be configured to provide knee motion therapy for rehabilitation.

For lower limb medical recovery, such as following knee surgery or injury, a patient often lies or is placed in a supine position, i.e. with the front (anterior) portion of the lower limb facing up and the back portion of the lower limb (posterior) facing down. As part of the recovery, it is often required for the lower limb to remain in a fixed position, being isolated and elevated, for a period of time. Also, elevating the lower leg may be desirable to ensure proper blood flow to reduce edema and deep vein thrombosis and promote healing. Other benefits from elevating the leg may be realized. Rotation of the foot may cause detrimental rotation of the lower leg. The twisting or torsioning effect on the leg may slow the process of healing, cause pain, or even cause further injury to the knee joint following injury or surgery. The disclosed support device avoids, minimizes, or reduces such problems by elevating a lower limb and immobilizing the foot and ankle to ensure proper leg position and healing.

Figure 1:
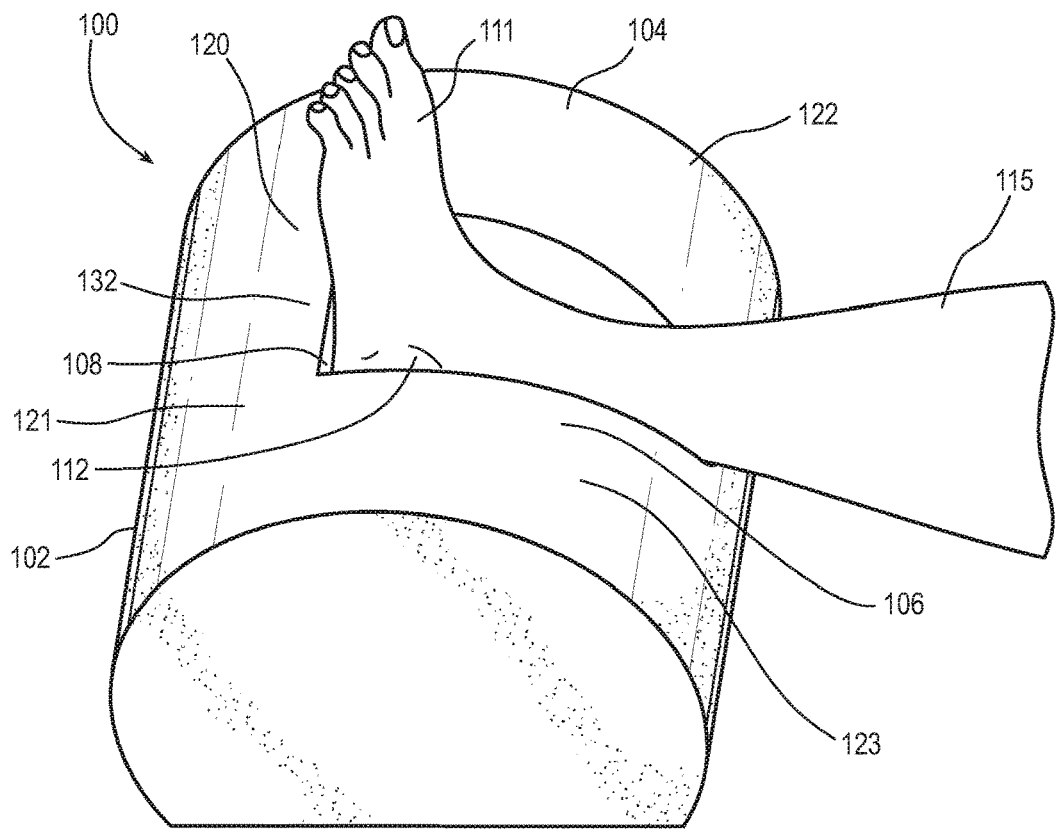
FIG. 1 is a perspective view of an exemplary use of a device having two lateral ridges and a medial depression between the ridges for lower limb elevation and foot immobilization, including restraint of foot rotation.

FIG. 1 illustrates an embodiment of a support device 100 for lower limb (e.g., foot, ankle, and knee) elevation and stabilization. Support device 100 comprises a main body 102 having a generally flat bottom surface, two spaced-apart lateral ridges 104, 106 extending upwardly along or near lateral edges of main body 102, and a medial depression 108 between lateral ridges 104, 106, which provides a support surface 118 on which a foot 111, including ankle 112 and heel 113 of a patient (FIG. 2), can be positioned. Importantly, support device 100 has a single medial depression that comfortably receives and supports a single foot while permitting independent, unobstructed movement of the patient's other foot and leg to maximize comfort and healing of the affected leg and avoid improper restraint of the unaffected leg.

Lateral ridges 104, 106 include inner side surfaces 114, 116 extending upward from support surface 118 that contact foot 111 when placed on support surface 118 within medial depression 108 and restrain medial and/or lateral rotation of foot 111. Lateral ridges 104, 106 further include distal upper surfaces 120, 121 and proximal upper surfaces 122, 123 on left and right sides of main body 102, respectively.

Foot 111 may face generally upward with toes pointing upward, as shown. However, foot 111 may be tilted or angled, with a side of foot 111 resting against one of inner side surfaces 114, 116. Lateral ridges 102, 104 may be spaced to provide a tight fit or a relaxed fit holding foot 111. Furthermore, medial depression 106 may be spaced with ample wiggle room to the extent that that an ankle need not fully touch inner side surfaces 114, 116.

From main body 102 with generally flat bottom surface, lateral ridges 104, 106 extend generally vertically upward and are located near or at along sides of main body 102. Lateral ridges 104, 106 may span a desired distance along the width of main body 102, or they may span an entire side of main body 102. In some embodiments, lateral ridges 104, 106 have lengths that extend beyond one or more main body edges, creating an overhang wall formation.

Figure 2:
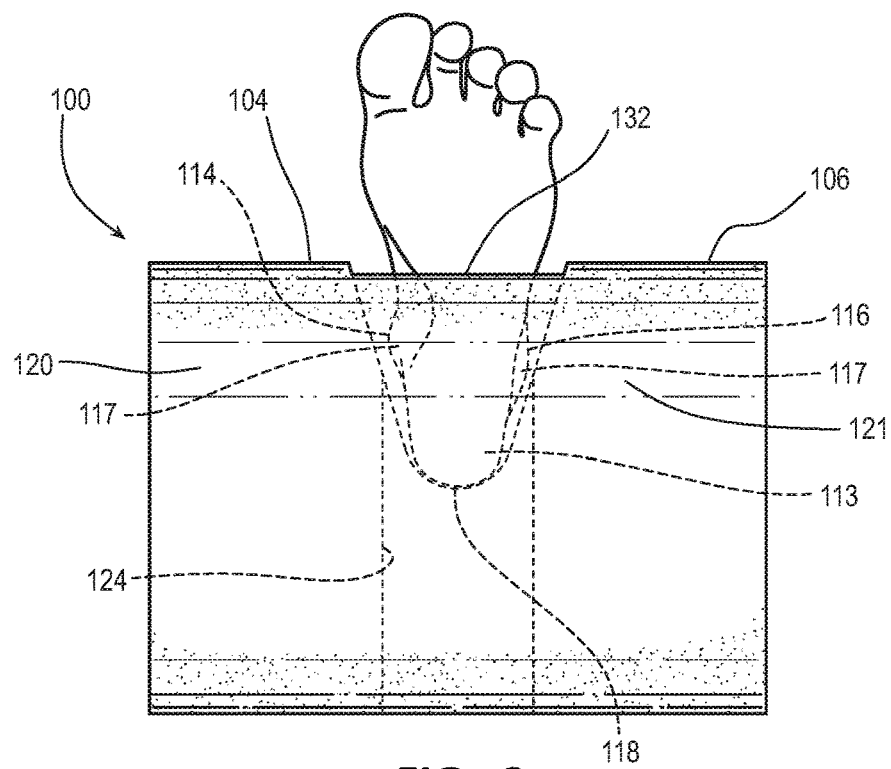
FIG. 2 is a rear elevation view of the device of FIG. 1 used in supporting and immobilizing a foot to restrain foot and lower leg rotation.

Lateral ridges 104, 106 can be integrally formed or interlocked with main body 102 in a manner that ensures they remain in an upright position during use to restrain lateral or medial rotation of foot 111. Lateral ridges 104, 106 can extend beyond (e.g., above) support surface 118 to a height so that a significant portion (e.g., ⅓, ½, or ⅔) of the foot is adjacent to side surfaces 114, 116 during use (as illustrated in FIG. 2). In some embodiments, lateral ridges 104, 106 can extend above support surface 118 by at least 3 inches, at least 3.5 inches, at least 4 inches, at least 4.5 inches, at least 5 inches, at least 5.5 inches, or at least 6 inches.

As shown, the support device can include a continuous medial ridge 132 that is continuous with lateral ridges 104, 106. In an alternative embodiment, medial ridge 132 may not be continuous with lateral ridges 104, 106. Medial ridge 132 may have a similar width corresponding to widths of lateral ridges 104, 106. Alternatively, the width of medial ridge 132 may vary. Medial ridge 132 may have a similar height as lateral ridges 104, 106 as shown. Alternatively, medial ridge 132 may have a greater or lesser height than lateral ridges 104, 106 to increase or decrease plantarflexion of ankle 112. Increasing the height of medial ridge 132 relative to lateral ridges 104, 106 provides greater restraint of plantarflexion of ankle 112, while decreasing the height of medial ridge 132 permits greater plantarflexion of ankle 112.

As illustrated in FIGS. 1 and 2, foot 111 is shown with heel 113 positioned in a distal section 125 of support surface 118. Distal section 125 can include a heel aperture 124 extending through main body 102 to an opening through bottom surface 126. Also, sides of ankle 112 are shown in contact with inner side surfaces 114, 116 of lateral ridges 104, 106.

As illustrated or suggested by FIG. 2, lateral ridges 102, 104 can have a height such that least half of the foot (by length) is flanked on each side by inner side surfaces 114, 116. Foot 111 as illustrated is of standard length (e.g., an average adult foot having a length of about 10-11 inches, or about 25-28 centimeters). The height of lateral ridges 104, 106 above support surface 118 can be selected so that at least ⅓, at least ½, or at least ⅔ of a foot of average length is flanked by inner side surfaces 114, 116. To accomplish this, lateral ridges 104, 106 can extend above support surface 118 by at least 3 inches, at least 3.5 inches, at least 4 inches, at least 4.5 inches, at least 5 inches, at least 5.5 inches, or at least 6 inches. Nevertheless, lateral ridges 104, 106 are advantageously shorter than a foot of standard length (e.g., an average adult foot length) to provide ventilation to the foot, including unrestricted ventilation of the upper foot, permit freedom of movement of the toes, and facilitate ready access to the foot, such as to provide triage.

When foot 111 exerts rotational forces to inner side surfaces 114, 116, such forces are transferred by one or both of lateral ridges 104, 106 to bottom surface 126 of main body 102, which transfers forces to a surface upon which main body 102 is placed. Bottom surface 126 of main body 102 is advantageously sufficiently wide ensure that main body 102 does not significantly rotate in response to forces applied by foot 111. In some embodiments, bottom surface 126 can have a width from left to right of at least 6 inches, at least 7 inches, at least 8 inches, at least 9 inches, at least 10 inches, at least 11 inches, or at least 12 inches.

FIG. 1 illustrates foot 111 and a distal end of a lower limb 115 distal to the calf muscle being supported by support surface 118. The distal end of lower leg 115 is also shown in contact with inner side surfaces 116, 114. Only the foot and distal end of a patient's leg is being supported in support device 100. The calf is not supported but is suspended by device 100 above a support surface on which device 100 rests. This configuration permits the patient's knee (not shown) to remain in a more extended rather than bent position and eliminates, minimizes, or reduces forces pressing against the calf muscle.

Figure 5:
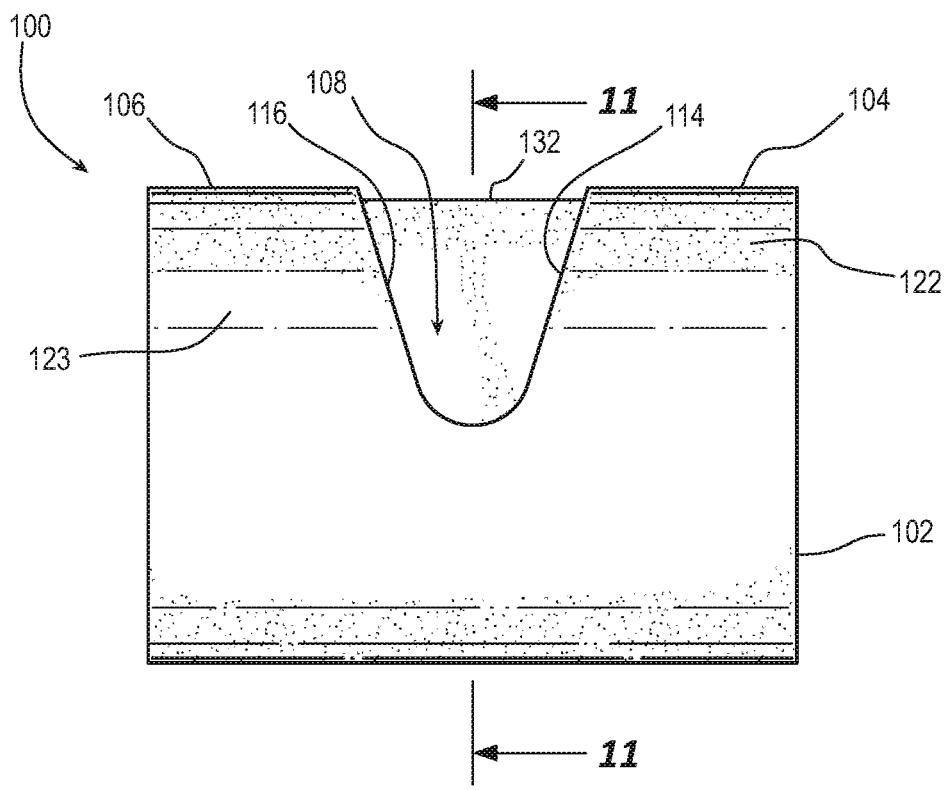
FIG. 5 is a front elevation view of the device of FIG. 1.
Figure 6:
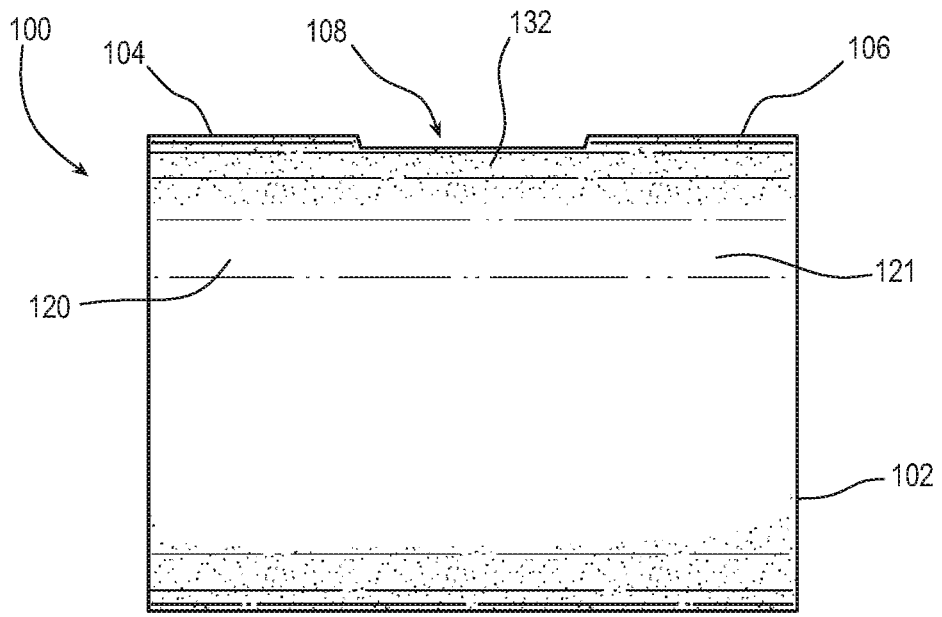
FIG. 6 is a rear elevation view of the device of FIG. 1.
Figure 7:
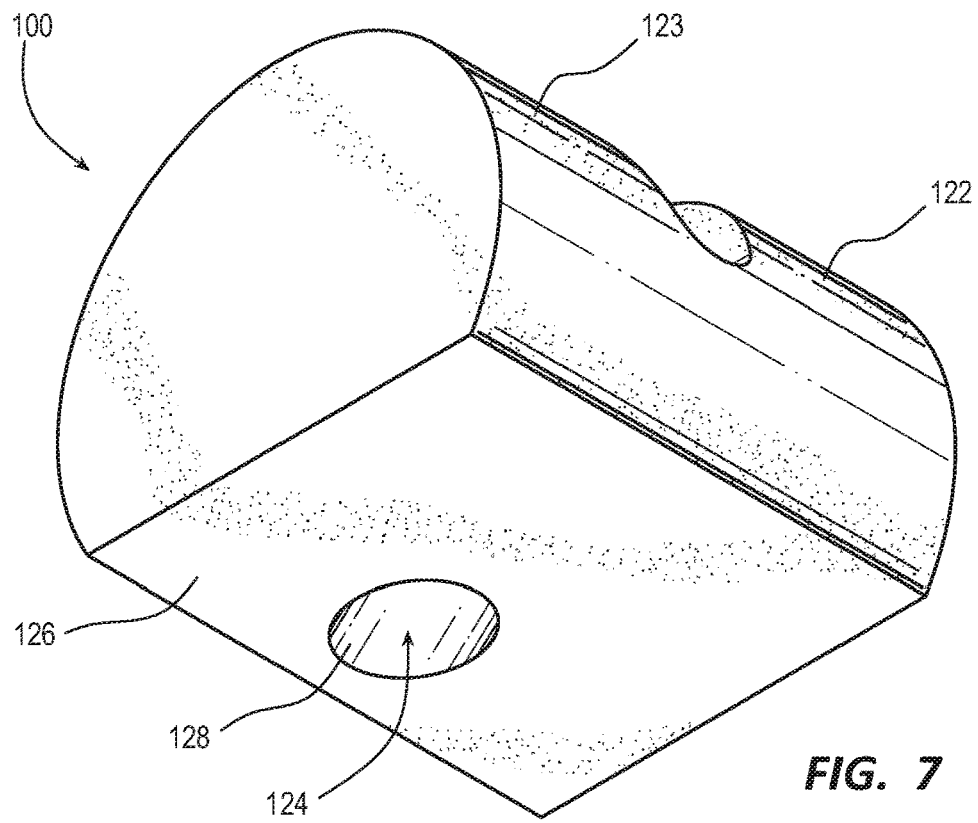
FIG. 7 is a bottom front perspective view of the device of FIG. 1.
Figure 8:
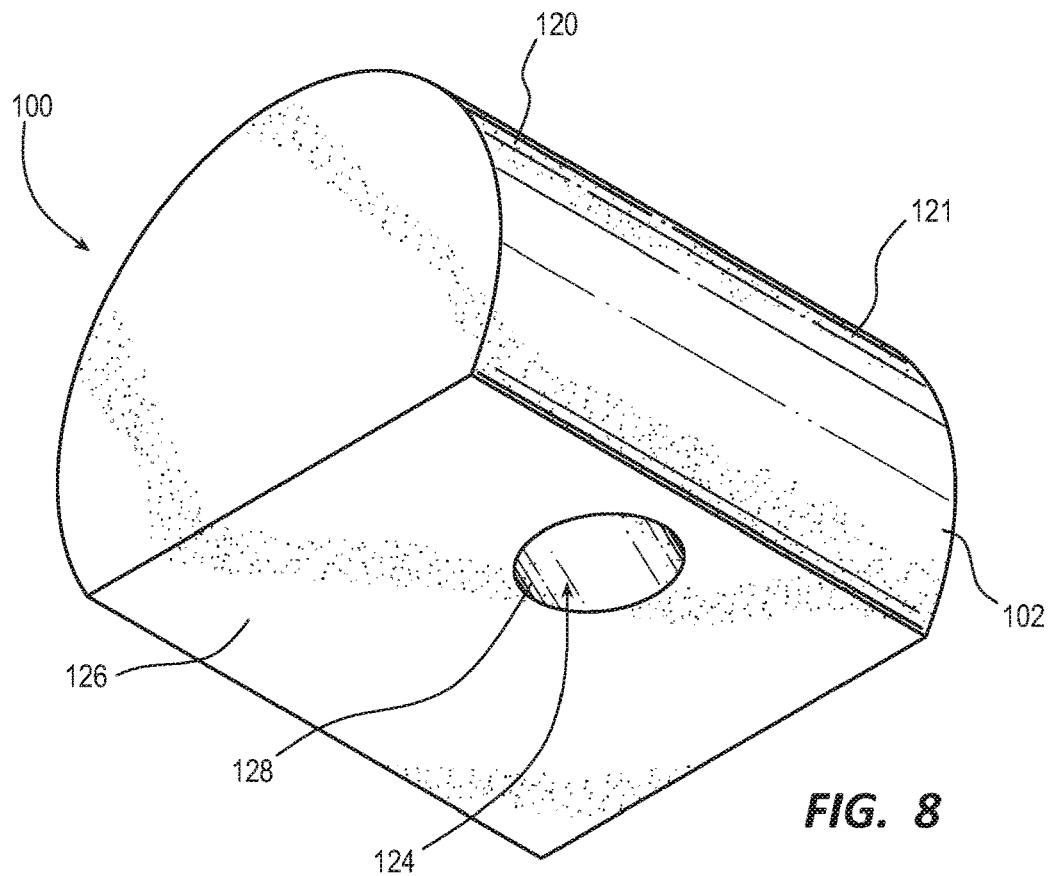
FIG. 8 is a bottom rear perspective view of the device of FIG. 1.
Figure 9:
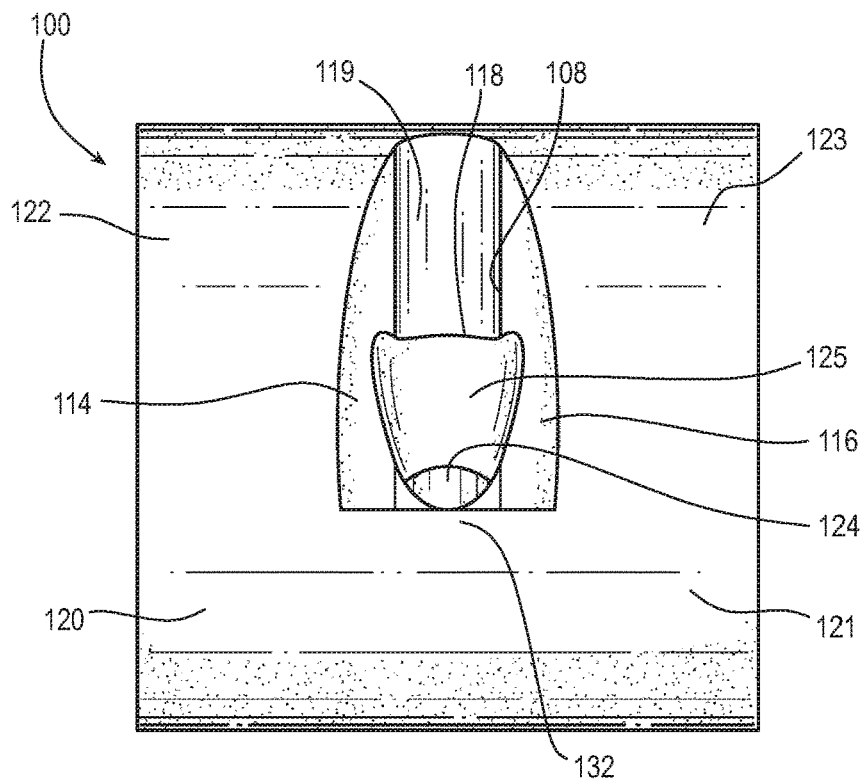
FIG. 9 is a top plan view of the device of FIG. 1.
Figure 10:
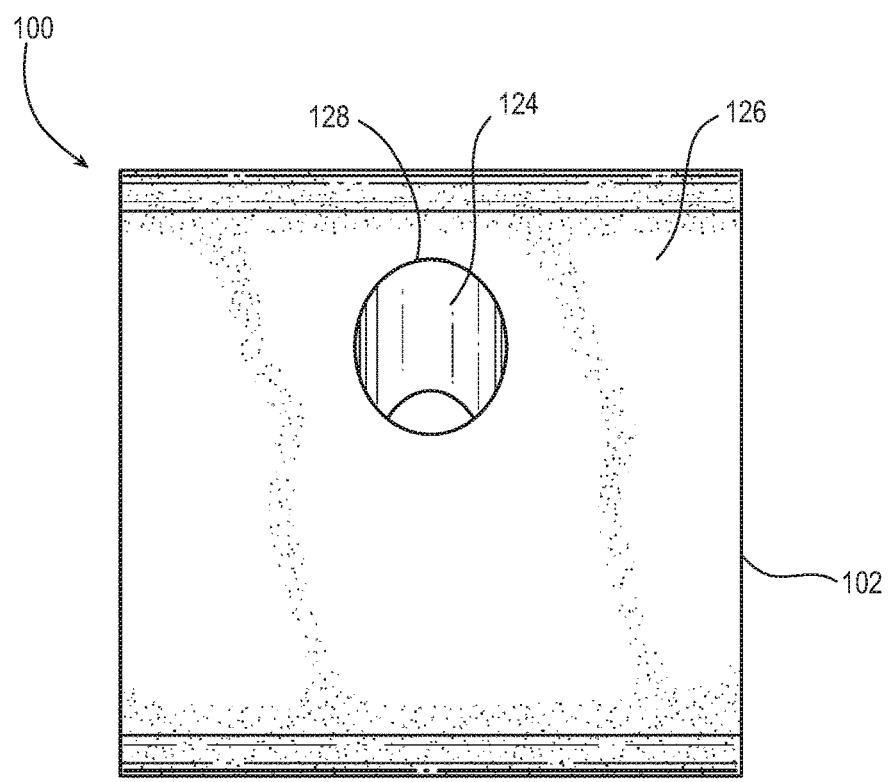
FIG. 10 is a bottom plan view of the device of FIG. 1.
Figure 11:
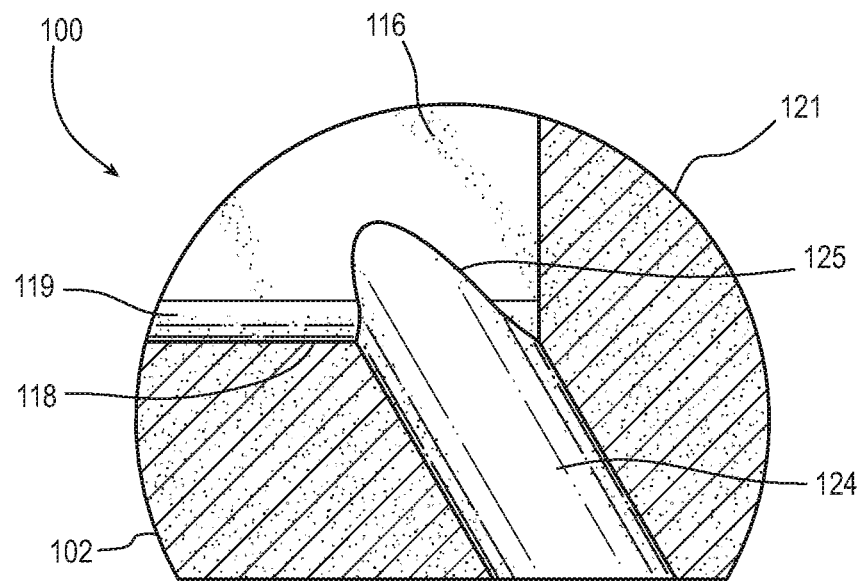
FIG. 11 is a left side cross-section view of the device of FIG. 1.

FIG. 2 illustrates support device 100 with foot 111 positioned therein so that ankle 112 rests on support surface 118. Support surface 118 can comprise an opening to a heel aperture 124 in which heel 113 can be positioned. Heel aperture 124 can extend through main body 102 to an opening 128 on bottom surface 126 (e.g., FIGS. 5-6). Support surface 118 can be sized to allow heel 113 to be inserted into heel aperture 124 to an appropriate depth (e.g., until ankle 112 comes comfortably into contact with support surface 118) to adequately support, retain, and effectively immobilize the foot to prevent rotation of the limb.

Heel aperture 124 may have a continuous diameter or varying diameter and may extend at an angle from an opening in the medial depression near support surface 18. Heel aperture 124 accommodates differently sized heels and reduces or eliminates underlying pressure on heel 113 to prevent formation of long-term heel sores. In this way, the heel itself does not bear the weight of the patient's leg, which can instead be borne by one or more of ankle 112, Achilles tendon, and/or lower leg 115 below the calf muscle. Heel aperture 124 can provide the additional benefit of ventilating heel 113 and ankle 112, permitting sluffed off skin to fall away from foot 111 to prevent infections and bad odors, and promote firm placement of a foot within the support device to immobilize the knee.

Figure 3:
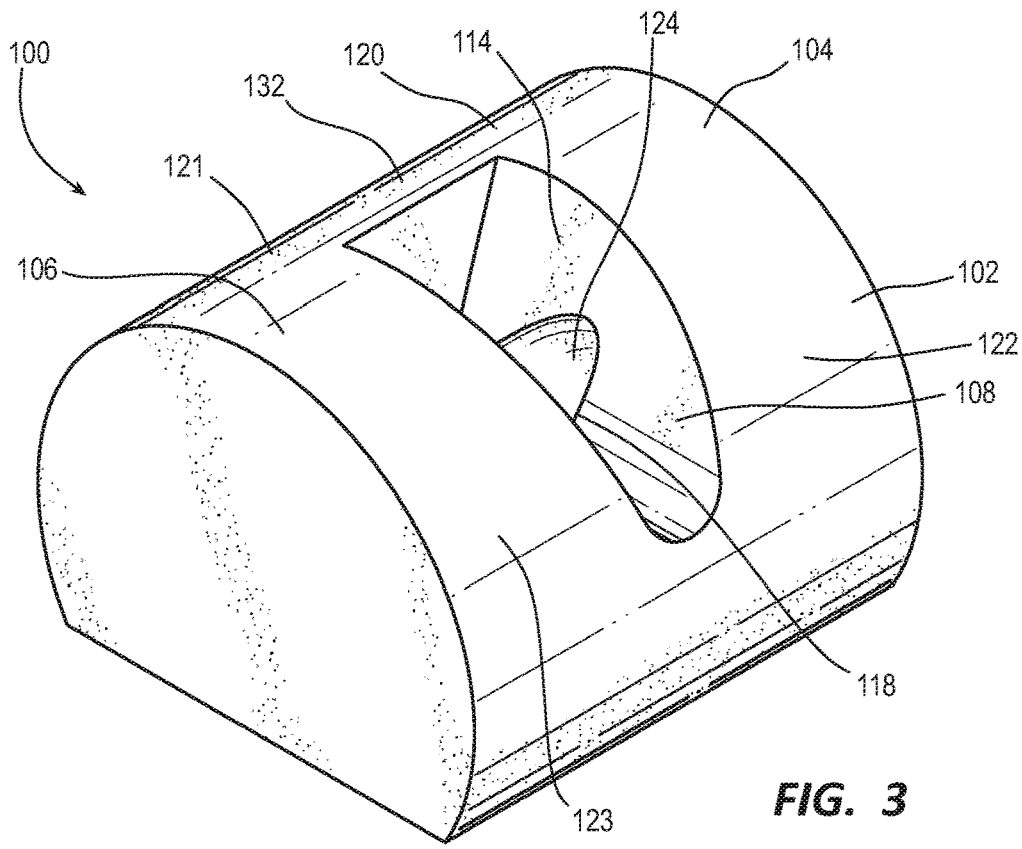
FIG. 3 is a top, front perspective view of the device of FIG. 1.
Figure 4:
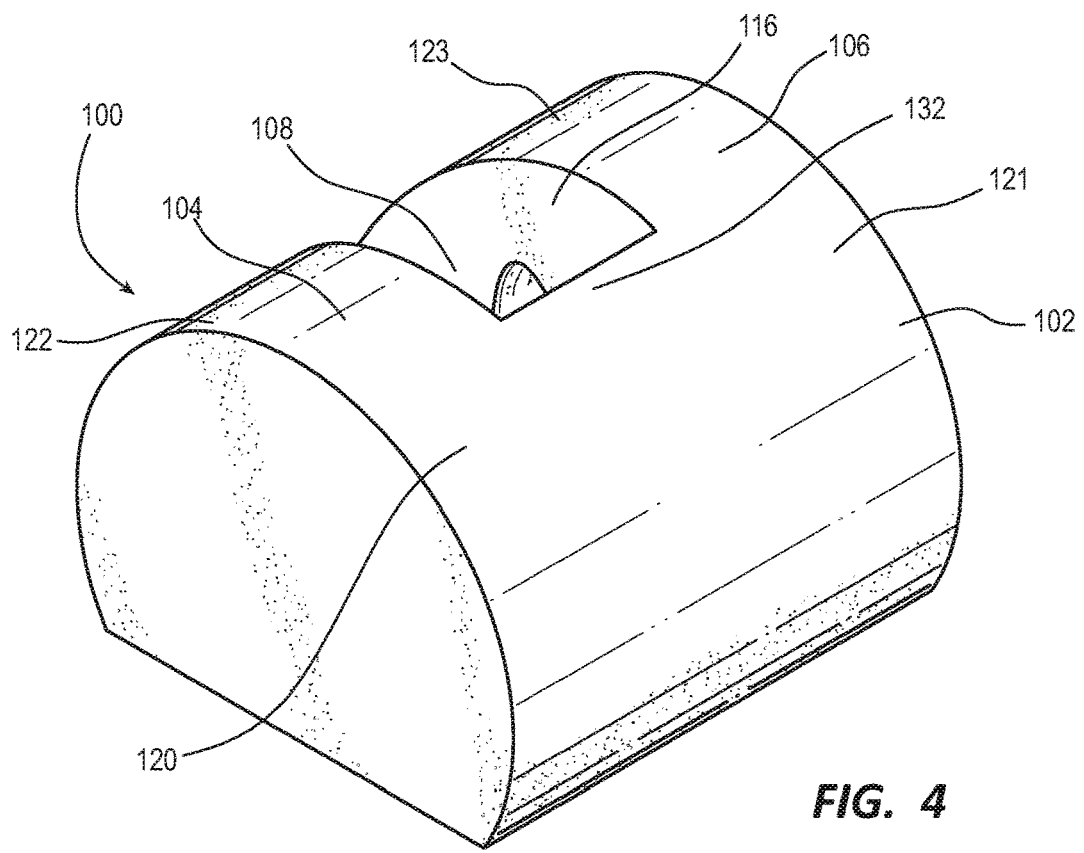
FIG. 4 is a top, rear perspective view of the device of FIG. 1.

FIGS. 3 and 4 illustrate support device 100, main body 102, lateral ridges 104, 106, medial depression 108, support surface 118, and inner side surfaces 114, 116. As illustrated, main body 102 may include a generally rectangular body. Alternatively, the shape of main body 102 may be multi-sided with sharp or rounded corners, such as rectangular, trapezoidal, or rectilinear, oblong, oval, circular, or have other shapes, proportions, and dimensions. The length may be larger than the width or, alternatively, the width may be larger than the length. Edges may be defined with sharp edges, curved edges, or a combination thereof.

The width, or wall thickness, of lateral ridges 104, 106 may be the same or they may vary. In some embodiments, at least one of lateral ridges 104, 106 can have a thickness of at least 0.75 inch, at least 1 inch, at least 1.25 inch, at least 1.5 inch, at least 1.75 inch, at least 2 inches, at least 2.25 inches, at least 2.5 inches, at least 2.75 inches, or at least 3 inches. Although lateral ridges 102, 104 are shown having similar widths and spanning main body 102 in a parallel manner, their widths may have varying dimensions such that one or more of inner side surfaces 104, 106 extends in a path that is not truly crosswise. For example, the width between inner side surfaces 114, 116 may be narrowed or tapered inwardly near or at a region where ankle 112 would be located on support surface 118 (FIGS. 1-2). Alternatively, the width between inner side surfaces 114, 116 may be tapered outward from a center region where ankle 112 would be located on support surface 118.

Support surface 118 may be contoured to conform to, e.g., contact and support, one or more of the lower leg distal to the calf, ankle region, and talus bone of the patient. To conform to the lower leg, ankle region, and talus bone of the patient, inner side surfaces 114, 116 may have notches, or hollowed out cavities, near the center where ankle 112 is located on support surface 118 when placed in depression 108. Alternatively, or additionally, inner side surfaces 114, 116 can have a vertical hollowed out indention that forms a vertical hollow 117 on each inner side surface 114, 116 to accommodate the talus bone (FIG. 2). Providing a hollowed section, whether a cavity or vertical hollow, on each inner side surface 114, 116 allows support device 100 to be used for either a left foot or right foot.

Support surface 118 may be generally flat; however, embodiments include a variety of different surfaces, including a surface that is curved, rounded, wavy, concave, convex, slanted upward, curved upward, slanted downward, curved downward, as well as a variety of other surfaces. In some embodiments, support surface 118 is curved and slanted upward or downward, providing a curving slope that better conforms to the sides of ankle 112 when the foot is placed in depression 108. Support surface 118 can comprise a proximal section 119 and a distal section 125. Proximal section 119 can provide support for the ankle region of the lower leg. The ankle region can include the Achilles tendon and the medial and lateral malleolus.

Distal section 125 can comprise heel aperture 124, the opening of which can be configured to receive heel 113. Heel aperture 124 can provide an opening to accommodate heel 113, which is typically elevationally lower than the rest of the foot and ankle when the foot is in a supine position. This permits heel 113 of foot 111 to be sunken into heel aperture 124 below the level of depression 108, thereby providing a support surface 118 with a proximal section 119 supporting the ankle and/or ankle region and a second portion having heel aperture 124 to prevent direct contact with heel 113. This can help to further isolate the heel from movement and thereby further restrain leg, foot, and ankle rotation (medial and/or lateral), as well as allowing support surface 118 to comfortably support the natural contours of the ankle. Heel aperture can provide ventilation to heel 113 and ankle 112 and provide a location where skin from the foot, ankle and heel can sluff off and not remain in the contact therewith.

In some embodiments, at least a portion of a distal upper surface of one of the spaced-apart lateral ridges 104, 106 can have a downward slope declining towards a proximal end.

As shown, both distal upper surfaces 120, 121 have downward slopes. In other embodiments, only one distal upper surface may have a downward slope.

In some embodiments, at least a portion of a proximal upper surface of one of the spaced-apart lateral ridges 104, 106 can have a downward slope declining towards a proximal end. As shown, both proximal upper surfaces 122, 123 have downward slopes; however, in some embodiments, only one proximal upper surface may have a downward slope.

The downward slope may be a curved, or rounded, downward slope. The combined proximal upper surfaces 122, 123 and distal upper surfaces 120, 121 may form an upside down, cupping shape. Any suitable shape may be provided, however. For example, instead of a curved shape, the combined upper surfaces may be generally flat, creating a standard wall appearance.

Outer edges of the proximal upper surfaces 122, 123 and distal upper surfaces 120, 121 may be sharp, blunt, or be rounded and smoothed out. For height, lateral ridges 104, 106 may have the same or similar height; however, their heights may differ. Also, there may be differences in curvatures and edges, shapes, length, and width. The height of lateral ridges 104, 106 and/or width between inner side surfaces 114, 116 can be selected to accommodate a foot of any size. For smaller feet, the height of lateral ridges 104, 106 and/or width between inner side surfaces 114, 116 can be reduced. For larger feet, the height of lateral ridges 104, 106 and/or width between inner side surfaces 114, 116 can be increased.

One or both of lateral ridges 104, 106 may extend generally vertically upward to a height of at least a significant portion (e.g., at least ⅓, at least ½, or at least ⅔) a general foot length according to anatomical measurements of a standard person (e.g., an average-sized adult foot). In this way, inner side surfaces 114, 116 of lateral ridges 104, 106 can abut the sides of a patient's foot 111 and thereby restrain medial and/or lateral rotation. A standard person is a mathematical model of a person based on any suitable data that simulates a person's size, body proportions, and the like, preferably based on adults. The model can be based upon data, for example, used in the clothing and shoe industry to define sizes for apparel and the like. The standard person used and the data set used to derive the standard person is chosen with the user of support device 100 in mind (typically adults) and can be based upon average values of body proportions from any sample of the population from, for example, total population, gender, age, body size or weight, nationality, or the like. The standard person may also be based upon any particular individual, or group of individuals. Thus, the standard person for a particular support device 100 may be designed for marketing to the public in general, or be customized to fit a particular group of people, or to fit an individual.

As illustrated in FIGS. 1-6 and 9, lateral ridges 104, 106 and side surfaces 114, 116 of support device 100 can be spaced apart sufficiently to permit a foot to be placed downwardly into or lifted upwardly out of medial depression 108 without having to manually manipulate the support device (e.g., without manually spreading apart lateral ridges 104, 106 when inserting a foot into or removing it from medial depression 108). This ease of insertion and removal helps prevent injury to the patient's knee. As also illustrated, support device 100 is devoid of any walls that contact the top (or anterior surface) of foot 111 placed in medial depression 108, which could limit potentially desirable foot movements, such as dorsiflexion, toe flexion, circumduction, eversion, or inversion, and limit ready access to the anterior foot region. In many cases, it may be desirable to permit dorsiflexion, or both plantarflexion and dorsiflexion, in order to permit therapeutic range of motion and prevent or reduce numbness or stiffness of the foot during healing of the knee.

In some embodiments, support surface 118 and/or medial depression 108 may by adjustable such that the space between them may be increased or decreased, as needed. For example, the lateral ridges 104, 106 may be moved inwardly or outwardly along main body 102 to form a smaller or larger space, respectively. Alternatively, inserts may be added and removed to either or both of inner side surfaces 114, 116 to change the size of medial depression 108. Appropriate attachments for adjustments may include screws, clamps, straps, and other means commonly known in the art.

Turning to FIGS. 7-12, heel aperture 124 can extend from distal section 125 of support surface 118 through main body 102 and terminate at an opening 128 in bottom surface 126. Heel aperture 124 can create a pressure-less heel pocket where heel 113 can be freely suspended and in which a heel of any shape or size can protrude into and rest within when a foot is positioned in medial depression 108 of support device 100. Even the softest surface can become uncomfortable and can strain or place pressure on tissue when a limb remains within medial depression 108 of support device 100 for an extended period of time. Heel aperture 124 may advantageously prevent heel sores, bruising, or other general discomfort typically resulting from remaining in one position for a prolonged period of time. Heel aperture 124 also provides increased ventilation of the foot and ankle and permits sluffing off of skin.

Figure 12:
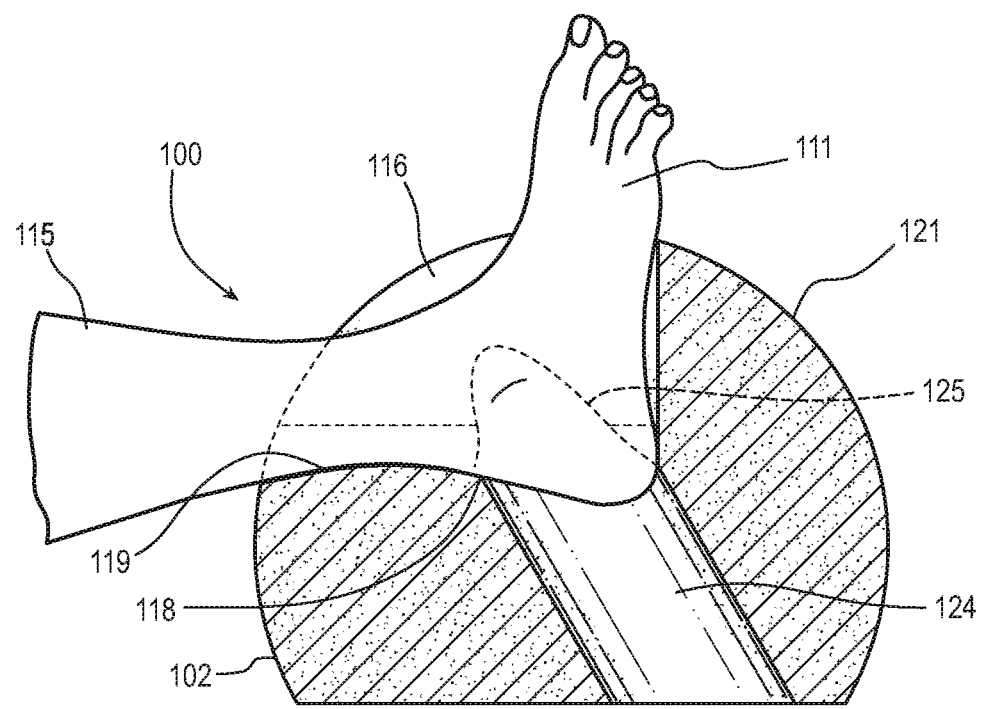
FIG. 12 is a left side cross section view of the device of FIG. 1 used in supporting and immobilizing a foot to restrain foot and lower leg rotation.

As shown in FIG. 12, a foot 111 in medial depression 108 of support device 100 can be positioned so that 112 rests on proximal section 119 of support surface 118, while heel 113 rests within heel aperture 124. The depth provided by heel aperture 124 may allow a limb to be supported and immobilized more securely by permitting a heel of any size to sink to an appropriate depth until the rest of ankle 112 contacts support surface 118. In apparatus that include a heel support surface rather than heel aperture 124, the surface is limited as to the shape of heel it can effectively restrain. For example, a heel with a heel spur may not allow a foot to rest flush with a support surface if a heel-receiving space is not sized to the correct depth, and a patient with foot inflammation, such as plantar fasciitis, may experience severe discomfort resulting from prolonged contact with a support surface. Furthermore, a patient may experience discomfort if the heel cannot rest fully within a support apparatus.

Support device 100 can mitigate these problems by providing a continuous receiving space due to the inclusion of heel aperture 124. Heel aperture 124, as shown in the Figures, can extend away from the heel at an angle and terminate at an opening 128 at bottom surface 126. This angulation can beneficially enhance airflow and ventilation to a patient's foot positioned within support device 100. The angled direction of heel aperture 124 also provides a graduated support surface 108 for the portion of foot 111 where ankle 112 and heel 113 meet, while still providing sufficient depth to comfortably position and suspend heel 113. In other embodiments, heel aperture 124 can extend straight down to bottom surface 126 rather than at an angle.

Additional materials may be added to provide further support, compression, structure, and weight. For example, cushioning may be added along inner side surfaces 114, 116 of lateral ridges 104, 106 to provide a snug or tight fit when a foot 111 is inserted within medial depression 108. Cush-ioning may be added in select areas along inner side surfaces 114, 116 of lateral ridges 104, 106 that abut sides of the patient's foot, for example, near or at the location where the ankle and heel are to be placed. Alternatively, cushioning may be added on only one side, either inner side surface 114 of lateral ridge 104 or inner side surface 116 of lateral ridge 106. Again, cushioning may be added in select areas, either at or near the location where the ankle and heel are to be placed or surrounding the location where the ankle and heel are to be placed. Cushioning may be added with cutaways or surface definitions in the shape of a standard foot, ankle or heel corresponding to various positions anticipated for foot 111.

Those skilled in the art will appreciate that suspending heel 113 and supporting ankle 112 and lower limb 115 by support surface 118, and constraining foot 111 by inner side surfaces 114, 116, can minimize or prevent medial and/or lateral rotation of the patient's lower leg. With the foot, including ankle and heel, constrained by the device in this manner, it will be appreciated that medial and/or lateral rotational movements of the lower limb and foot can be minimized or prevented. For example, one, some or all of the following movements may be selectively permitted, minimized, or prevented:

Dorsiflexion: Bending the foot at the ankle toward the shin (bending the foot upward).
Plantarflexion: Bending the foot at the ankle toward the sole (bending the foot downward).
Eversion: Turning the foot so the sole faces laterally.
Inversion: Turning the foot so the sole faces medially.
Circumduction: Moving a part so that its end follows a circular path (moving the toes in a circular motion without significantly moving the ankle).

As shown in the Figures, support device 100 can include a medial ridge 132 positioned transversely between lateral ridges 104, 106, which can be included to limit plantarflexion of the foot during use. Medial ridge 132 may, in cooperation with ridges 104, 106, also help limit or restrict eversion, inversion and/or circumduction of the foot.

In addition to minimizing or preventing movements of the foot, the support device may prevent medial and/or lateral rotational movements of the knee and overall leg that may otherwise be caused by medial and/or lateral rotation of the foot. The knee is thus protected against torque caused by medial and/or lateral rotation of the foot. Also, the foot and knee may be restrained from turning medially (inwardly) or laterally (outwardly), ensuring that the knee does not face a direction other than a direction that is parallel to the direction of the foot. Further, the device supports the foot and ankle such that free space is created proximally to the ankle in the region of the Achilles tendon and calf muscle. This free space allows the leg to drop into full extension at the knee without raising the heel away from the device.

In preventing medial and/or lateral rotation, a leg may remain in a generally fixed position. Ice may be applied to a region of the leg to reduce swelling or ease pain. By providing stabilizing support and isolation, the leg is better able to get proper rest and healing. If the foot or leg require to be moved, for example, to help adjust body position or remove the patient from the table, the device keeps the process simple because it is easy to install and remove.

Different materials can be used to manufacture the device. For example, the main body may comprise open cell polymer foam. In some embodiments, the polymer foam can be coated with a flexible, fluid-impermeable polymer coating. Alternatives include that the device comprise radiolucent material. An advantage of open cell polymer foam is that it inherently resists slippage relative to a bed or other surface upon which is it placed. Alternatively, where sliding is desired, a smooth, low-friction surface or attachment may be provided on the bottom surface to facilitate sliding, such as for performing leg exercises.

The device may have a height and/or flexibility, coupled with sufficient firmness, to maintain a minimum elevation of the patient's ankle of at least 1 inch, at least 2 inches, at least 3 inches, or at least 4 inches, or at least 5 inches above the supporting surface during use. Providing stabilized elevation may be helpful in keeping the leg immobilized at a desired height during a period of medical recovery. The device can have a firmness, yet with sufficient softness and yield, to reduce pressure at and provide a comfortable support for sensitive soft-tissue areas.

The support device may optionally include an auxiliary pad configured to be positioned beneath the main body to further elevate the patient's ankle during use. This permits adjustments to the height or elevation of the support surface to accommodate specific needs of the patient. The auxiliary pad can be made from the same open cell foam material as the support device and can advantageously prevent inadvertent slippage of the support device relative to the auxiliary pad and also relative to a bed or other surface upon which is it placed.

When using the device to elevate the patient's ankle during medical recovery, a stable platform, such as a bed or hospital bed, may be provided. The device may be placed on an upper surface of the stable platform. Proper positioning of the device may include putting the device underneath the ankle region of the patient, thereby elevating the ankle of the patient.

Figure 13:
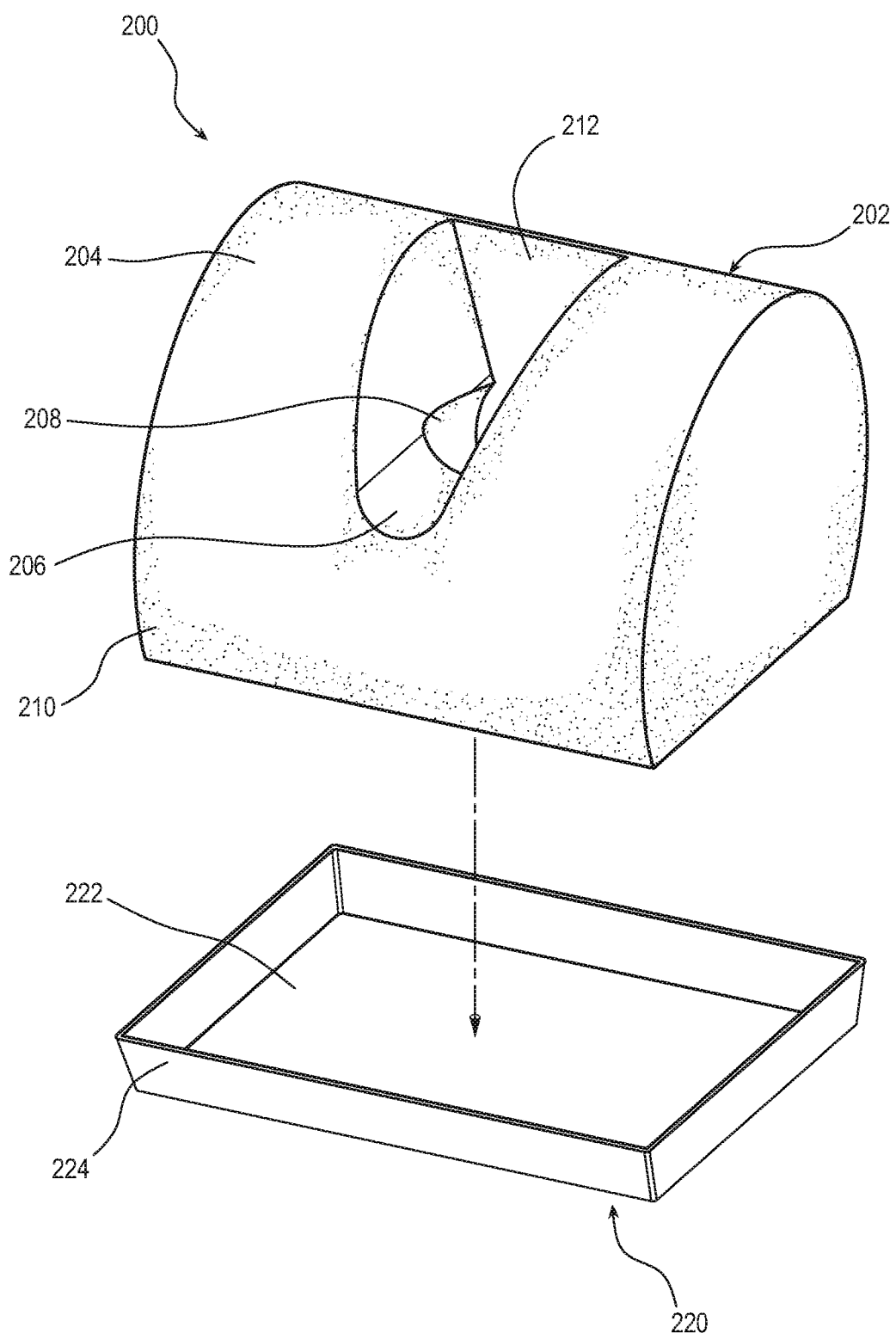
FIG. 13 is an exploded perspective view of an exemplary orthopedic device, such as the device of FIG. 1, with a low friction attachment.
Figure 14A:
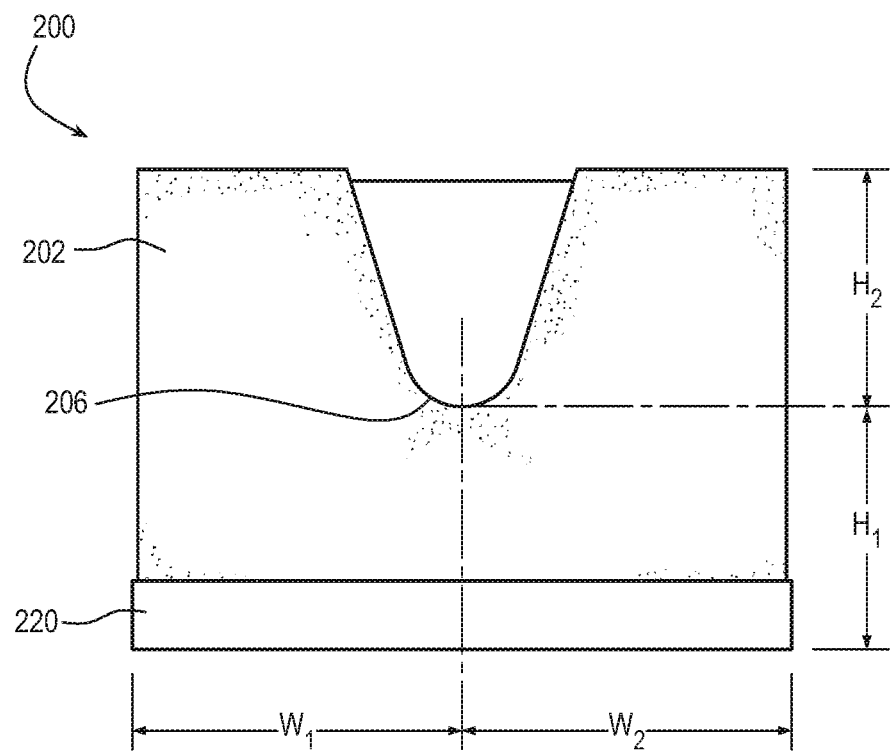
FIGS. 14A through 14E illustrate, respectively, front, back, top, bottom, and side views of the orthopedic device of FIG. 13.
Figure 14B:
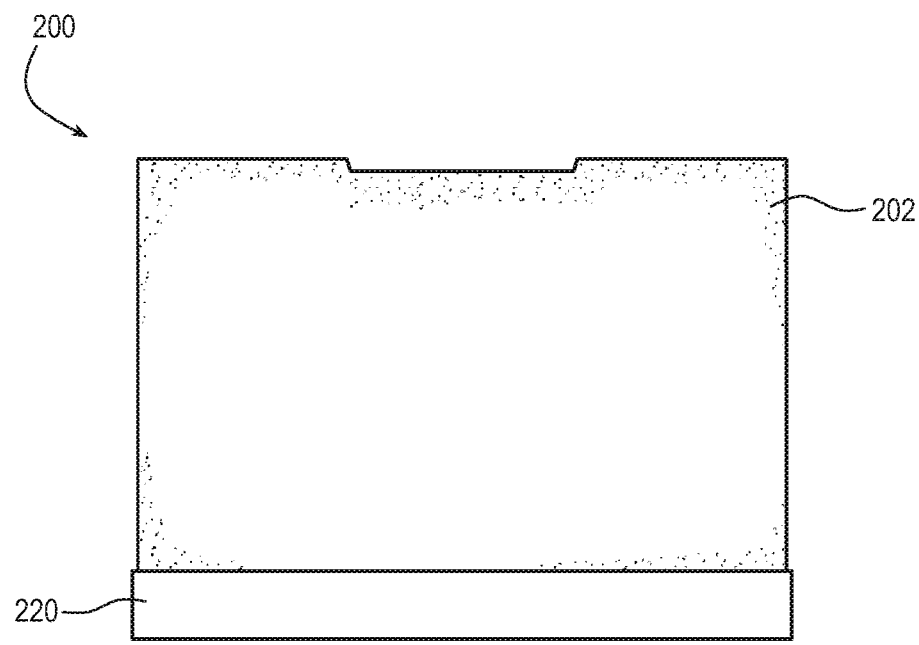
Figure 14C:
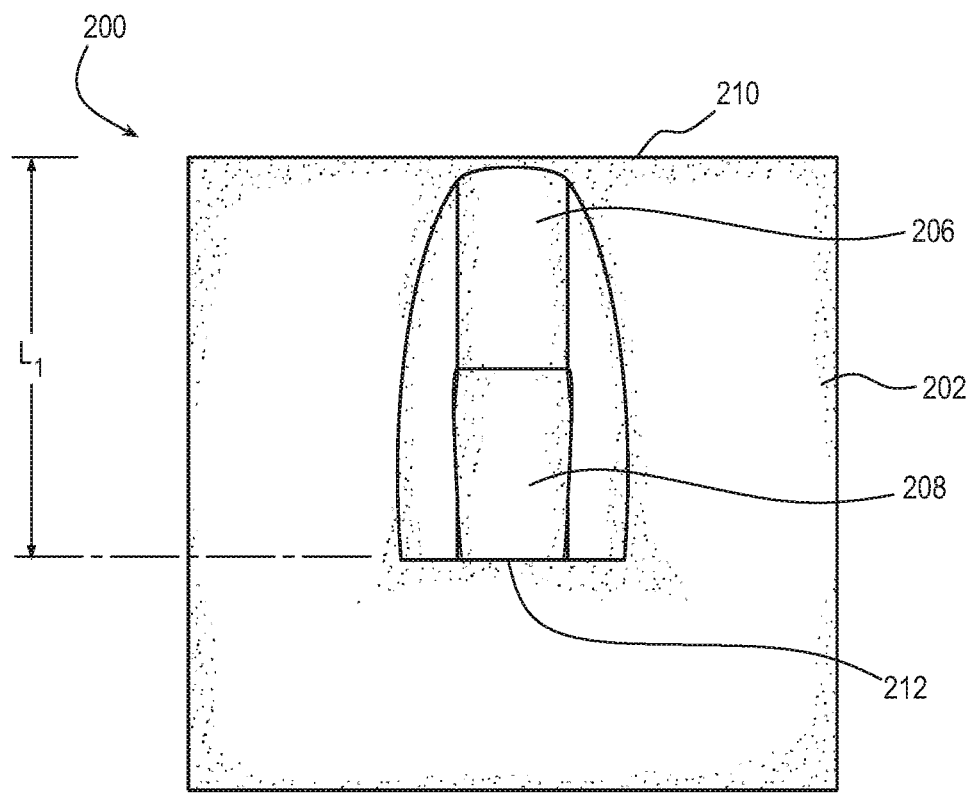
Figure 14D:
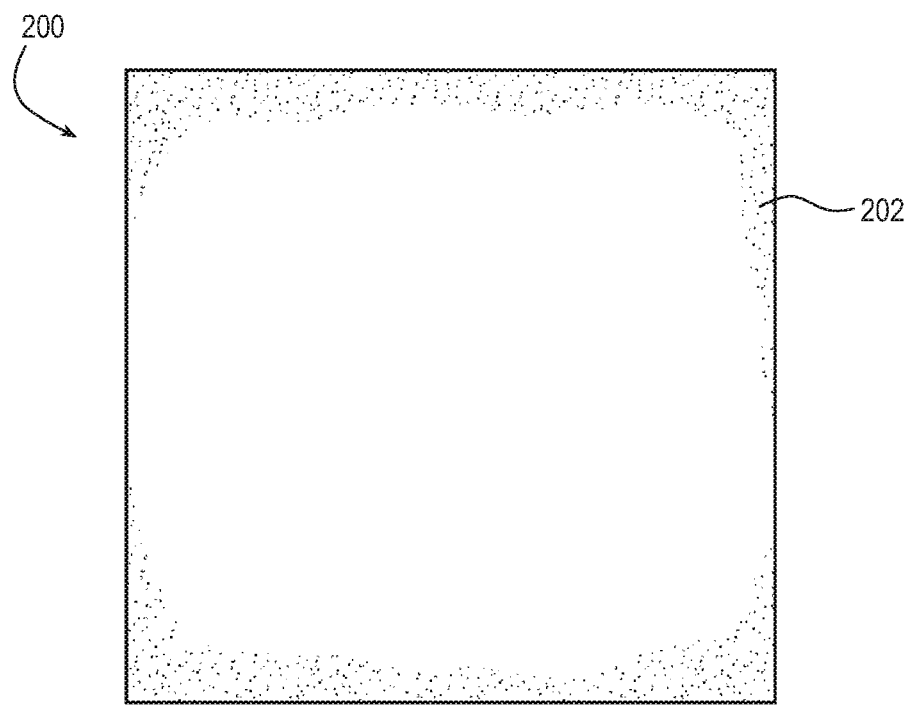
Figure 14E:
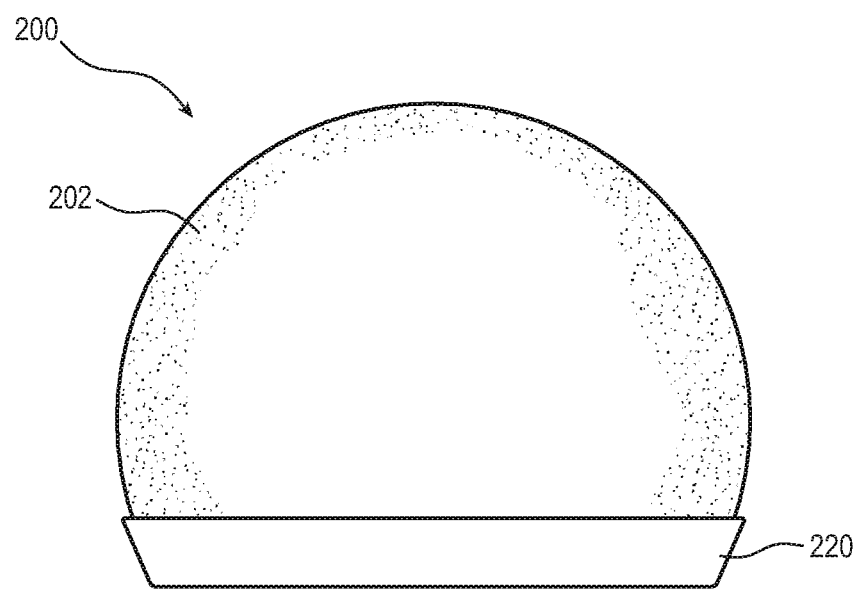
Figure 15:
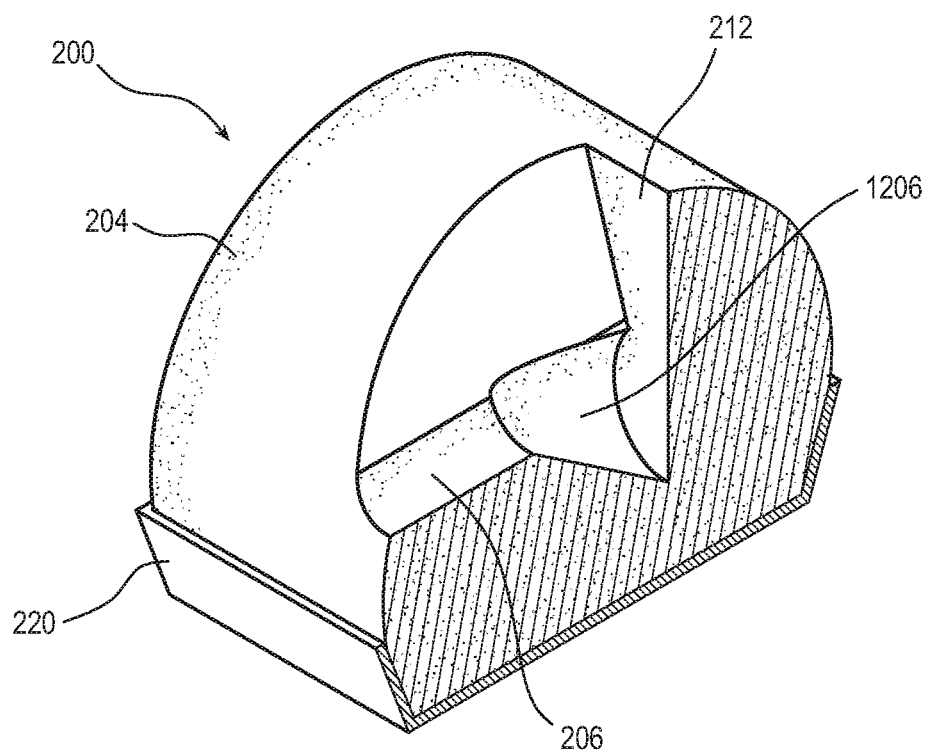
FIG. 15 illustrates a perspective cross-section view of the orthopedic device of FIGS. 13 and 14 to better illustrate an ankle support surface and heel support surface.

FIGS. 13-15 illustrate an alternative embodiment of an orthopedic support device 200 for lower limb elevation and stabilization, which also assists the patient in performing motion therapy exercises while still supporting and stabilizing the foot. Support device 200 includes a body 202 in which the patient's foot may be placed. Body 202 may include features similar to device body 102, including heel aperture 124 as described above and/or be similar to devices in U.S. Pat. Pub. No. 2020/0060917, which is incorporated by reference. Thus, although the following description illustrates an embodiment of a body 202 with a heel support surface 208 (rather than a heel aperture 124) in combination with a base 220, it will be understood that support device 100, including heel aperture 124, may be combined with base 220 in lieu of the specific body 202 described below.

Body 202 includes a pair of opposing, spaced-apart side ridges 204 that define a depression therebetween. The bottom portion of the depression forms an ankle support surface 206 and a heel support surface 208. Ankle support surface 206 extends proximally to front/proximal side 210 of device 200. Heel support surface 208 is located just distal of ankle support surface 206 and extends distally to a distal ridge 212 that extends between opposing side ridges 204. In some embodiments, distal ridge 212 may be omitted so that the depression is open at both proximal and distal sides of the device.

Ankle support surface 206, heel support surface 208, and inner sides of side ridges 204 can be configured in size and shape to contact and conform to the patient's foot when placed therein. As shown, heel support surface 208 has lower height than ankle support surface 206. This beneficially allows the heel of the patient's foot to sink down into heel support surface 208 and allows the ankle portion of the foot to contact ankle support surface 206. Ankle support surface 206 and heel support surface 208 therefore work in conjunction with each other to conform to the natural contours of the ankle and heel.

As shown, the inner surfaces of side ridges 204 can be tapered such that they are closer to one another near the bottom of the depression and further apart from one another closer to the top of the device. This flared/tapered profile can better conform to the natural shape of a foot, which has a wider anterior portion closer to the toes that narrows to the posterior portion at the heel. The depression is therefore configured in size and shape to contact and conform to Body 202 can be formed of a polymer foam material that further aids in cushioning and shaping to the contours of the patient's foot. The polymer foam material may be an open cell foam, such as polyurethane foam, although other suitable polymer materials may be utilized in addition to, or as an alternative to, polyurethane foam.

Orthopedic device 200 also includes a base 220 that is sized and shaped to attach to the bottom of body 202. In this embodiment, base 220 has a raised perimeter 224 that substantially matches the outline of the bottom of body 202 so that body 202 can be snugly placed within base 220. The bottom of body 202 and base 220 are depicted as having substantially matching rectangular shapes, but other embodiments may have other shapes, such as square shapes, other polygonal shapes, or circular, curved, or ovoid shapes.

A raised perimeter 224 extends upward from a bottom surface 222 of base 220. The height at which raised perimeter 224 extends above bottom surface 222 may be varied. Such height should be sufficient to provide a good interface with body 202 but should not be so high as to interfere with support functions of body 202 or so high as to be a waste of material. Providing raised perimeter 224 with a height of about 0.5 inches to about 2 inches, or about 0.75 inches to about 1.5 inches, has been found to provide effective results.

As mentioned above, bottom surface 222 can provide a low-friction surface for device 200 that enables the device to slide along the floor or other support surface during motion exercises performed by the patient while the patient's foot is supported therein. Base 220 can be formed from a polymer material with sufficient low-friction properties and hardness to facilitate sliding. In one embodiment, base 220 can be formed from polystyrene, though other suitable polymers may also be utilized (e.g., polytetrafluoroethylene, nylon, and the like). The material utilized to form base 220 preferably has a Shore durometer (e.g., Shore A) value of about 50 to about 90, more preferably about 60 to about 80.

Base 220 is preferably slightly smaller than the corresponding bottom portion of body 202. That is, raised perimeter 224 preferably forms an outline that is somewhat smaller than the perimeter/outline of the bottom of body 202. Because body 202 may be formed of a polymer foam material, this allows the bottom portion of body 202 to be somewhat compressed where inserted into base 220. This beneficially allows the bottom portion of body 202 to expand outward against the inner surfaces of raised perimeter 224, eliminating gaps and providing for a tight, snug fit. Such fit is particularly important for medical devices to avoid areas where debris or contaminants may get trapped and to allow for easier cleaning of the device. Body 202 may be coupled to base 220 using an adhesive.

Preferably, raised perimeter 224 is formed with bottom surface 222 such that the entire base 220 is one integral piece. Raised perimeter 224 provides additional benefits by preventing bottom surface 222 from catching or snagging while sliding around the floor during motion exercises. For example, without raised perimeter 224, the corners and/or edges of bottom surface 222 could be disposed on the bottom of the entire device itself, which could detrimentally be a point at risk of catching/snagging against parts of the floor while sliding along the floor.

Those skilled in the art will appreciate that supporting the heel and ankle with support surfaces 206 and 208 and by inner side surfaces of side ridges 204 can minimize or prevent medial and/or lateral rotation of the patient's lower leg, such as the movements discussed above (e.g., dorsiflexion).

In addition to minimizing or preventing foot rotation, the orthopedic device may prevent medial and/or lateral rotational movements of the knee and leg that may otherwise be caused by medial and/or lateral rotation of the foot. The leg and knee can thus be protected against torsional effects and torque caused by medial and/or lateral rotation of the foot. Also, the foot and knee may be restrained from turning medially (inwardly) or laterally (outwardly), ensuring that the knee does not face a direction other than a direction that is parallel to the direction of the foot. Further, the device supports the foot and ankle such that free space is created proximal of the ankle in the region of the Achilles tendon and calf muscle. This free space allows the leg to drop into full extension at the knee, which is beneficial for stretching the knee and promoting better range of motion.

FIGS. 14A through 14E illustrate front, back, top, bottom, and side views, respectively, of device 200. With reference to FIG. 14A, a first height "H1" is defined as the distance between the bottom of device 200 and the bottom of ankle support surface 206. Preferably, H1 is at least about 2.5 inches, or at least about 3 inches, or at least about 4 inches. For example, H1 may be about 2.5 inches to about 7 inches, or about 3.5 inches to about 6 inches. Heights within the foregoing ranges beneficially enable sufficient elevation of the ankle and heel with enough clearance to keep the posterior side of the knee from touching the floor so that gravity can encourage knee extension.

With continued reference to FIG. 14A, a second height "H2" is defined as the distance between the bottom of ankle support surface 206 to the top of side ridges 204. This distance is preferably at least about 2.5 inches, or at least about 3 inches, or at least about 3.5 inches, or at least about 4 inches. For example, H2 may be about 2.5 inches to about 6 inches, or about 3 inches to about 5.5 inches. Heights within the foregoing ranges beneficially enable sufficient cradling of the foot to prevent rotation. Lower heights are less preferred because the device has less ability to prevent the foot from rotating.

FIG. 14A also shows a first width "W1" and a second width "W2" defined as the distances between a vertical plane extending through the center of ankle support surface 206 and the respective sides of device 200. W1 and W2 are preferably independently at least about 2.5 inches, or at least about 3.5 inches, or at least about 4 inches, or at least about 4.5 inches, or at least about 5 inches. For example, W1 and W2 may independently be about 3 inches to about 9 inches, or about 4 inches to about 7 inches. Having widths within the foregoing ranges beneficially provides sufficient structure and width to prevent the entire device from tipping as a result of foot rotation.

Referring now to the top view of FIG. 14C, a length "L1" is defined as the distance between front/proximal surface 210 and distal ridge 212. The length L1 is preferably about 3 inches to about 11 inches, or about 4 inches to about 10 inches, or about 5 inches to about 9 inches, or about 6 inches to about 8 inches. Providing a length L1 within the foregoing ranges enables the patient's ankle and heel to be sufficiently and comfortably supported, but without overly supporting more proximal regions of the lower leg, which would reduce the suspending effect upon the knee joint. As explained above, keeping the knee sufficiently suspended beneficially aids in providing stretching toward the extended position.

FIG. 14E illustrates a cross-sectional view of device 200 to better illustrate some of the features of the depression, including ankle support surface 206, heel support surface 208, and the inner surface of side ridges 204. As described above, heel support surface 208 sinks lower than ankle support surface 206. Heel support surface 208 may slope/angle away from ankle support surface 206 as shown. Preferably, heel support surface 208, at its lowest, most distal point, is about 1.5 inches to about 3.5 inches lower than ankle support surface 206.

As explained herein, the disclosed orthopedic devices are configured to conform to and support a patient's foot. Clearly, foot size may vary among patients based on age, sex, and anatomical differences. As used herein, a "foot" should be understood to refer to a foot having a shoe size (United States) of about 7 to about 15, more commonly about 9 to 12, for men, and about 5 to 13, more commonly about 7 to 11, for women. Larger or smaller devices may also be scaled accordingly for those patient's with larger or smaller feet, respectively.

While certain embodiments of the present disclosure have been described in detail, with reference to specific configurations, parameters, components, elements, etcetera, the descriptions are illustrative and are not to be construed as limiting the scope of the claimed invention. Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

The invention claimed is:

1. A device for supporting and elevating a patient's foot and restraining medial and lateral rotation of the patient's foot, comprising:
   a main body including a bottom portion having a generally flat bottom surface and lateral edges;
   two spaced-apart lateral ridges extending along or near the lateral edges of the main body and having inner side surfaces;
   a medial depression between the lateral ridges that provides a support surface on which the ankle may be positioned and supported, wherein the support surface is contoured to support natural contours of the ankle, the support surface including a heel aperture sized to permit the heel to sink therein and be suspended without contacting the support surface; and a base attached to the bottom portion of the main body, the base having a generally flat low-friction bottom surface and a raised perimeter that extends upward from the bottom surface of the base and substantially matches an outline of the bottom portion so that at least part the bottom portion and lateral edges of the main body are placed within the base, wherein the low-friction bottom surface and raised perimeter of the base facilitate sliding of the device on a surface, and the main body supports and stabilizes the foot, while performing leg exercises, wherein the inner side surfaces of the lateral ridges limit medial and/or lateral rotation of the patient's foot when placed on the support surface of the medial depression, wherein the heel aperture assists in supporting, retaining, and immobilizing the foot when placed on the support surface.

2. The device of claim 1, wherein the lateral ridges each extend above a lowest portion of the support surface to a height of at least 3 inches to thereby confine and restrain a foot placed in the medial depression and limit or prevent medial and lateral rotation of the foot.

3. The device of claim 1, wherein the lateral ridges are spaced apart so as to facilitate downward placement of a foot into the medial depression without manual manipulation and spreading apart of the lateral ridges.

4. The device of claim 1, further comprising a medial ridge positioned transversely between the lateral ridges, distal to a heel of a foot placed in the medial depression, and extending to a height above the support surface of at least 3.5 inches to limit plantarflexion of the foot.

5. The device of claim 1, wherein the device is devoid of walls that contact an anterior surface of a foot placed in the medial depression.

6. The device of claim 1, wherein the device is devoid of walls that limit dorsiflexion of a foot placed in the medial depression.

7. The device of claim 1, wherein at least a portion of a proximal upper surface of at least one lateral ridge has a downwardly curving slope declining from an upper extent of the lateral ridge towards a lower extent of the lateral ridge at a proximal end of the device such that the at least one lateral ridge at least partially forms a curved shape.

8. The device of claim 1, wherein at least a portion of a distal upper surface of at least one lateral ridge has a downwardly curving slope declining from an upper extent of the lateral ridge towards a lower extent of the lateral ridge at a distal end of the device such that the lateral ridge at least partially forms a curved shape.

9. The device of claim 1, wherein the main body and lateral ridges comprise open cell polymer foam.

10. The device of claim 9, wherein the polymer foam is coated with a flexible, fluid-impermeable polymer coating.

11. The device of claim 1, wherein the inner side surfaces are contoured to receive and accommodate a talus bone of the patient.

12. The device of claim 1, wherein the medial depression is contoured to approximately fit the contour of a portion of a lower leg proximal to the ankle and distal to the calf.

13. The device of claim 1, further comprising an auxiliary pad configured to be positioned directly beneath the main body to further elevate the patient's ankle during use.

14. The device of claim 1, wherein the raised perimeter extends to height above the bottom surface of about 0.5 inch to about 2 inches.

15. An orthopedic device for elevating a patient's foot and restraining medial and lateral rotation of the patient's foot, the device comprising:

a main body, the main body including:
   a bottom portion having a generally flat bottom surface,
   two opposing side ridges that define a depression therebetween, and
   a support surface disposed between the opposing side ridges and configured to support an ankle and distal end of the patient's leg and terminate distal to the patient's calf when the patient's foot is placed within the orthopedic device, wherein the opposing side ridges are configured to conform to the patient's foot to stabilize the foot and prevent medial and lateral rotation of the foot, wherein the side ridges extend to a height of at least three inches above the ankle support surface and are spaced apart so as to facilitate downward placement of a foot into the medial depression and upward lifting of the foot from the medial depression without manual manipulation and spreading apart of the side ridges; and a base attached to the bottom portion of the main body, the base having a generally flat low-friction bottom surface and a raised perimeter that extends upward from the bottom surface of the base so that at least part of the bottom portion of the main body is placed within the base, wherein the low-friction bottom surface of the base facilitates sliding of the device on a surface, and the main body supports and stabilizes the foot, while performing leg exercises, wherein the opposing side ridges limit medial and/or lateral rotation of the patient's foot when placed on the support surface of the medial depression.

16. The device of claim 15, wherein the main body further comprises a heel support surface distal of the ankle support surface and that extends lower than the ankle support surface.

17. The device of claim 15, wherein the main body further comprises a heel aperture.

18. The device of claim 15, wherein the main body further comprises a distal ridge extending between the two opposing side ridges and disposed distal of the ankle support surface, wherein the distal ridge extends to a height of at least three inches above the ankle support surface.

19. The device of claim 15, wherein the base is slightly smaller than the bottom portion of the main body such that the bottom portion of the main body is encompassed and compressed when positioned within the base.

20. The device of claim 15, wherein the perimeter of the base facilitates sliding of the device on a surface without catching or snagging.

21. A device for supporting and elevating a patient's foot and restraining medial and lateral rotation of the patient's foot, comprising:

a main body, the main body comprising:
   a bottom portion having a generally flat bottom surface and lateral edges;
   two spaced-apart lateral ridges extending along or near the lateral edges of the main body and having inner side surfaces, wherein the lateral ridges are spaced apart so as to facilitate downward placement of a foot into the medial depression and upward lifting of the foot from the medial depression without manual manipulation and spreading apart of the lateral ridges; and a medial depression between the lateral ridges that provides a support surface on which the ankle may be positioned and supported, wherein the support surface is contoured to support natural contours of the ankle, and wherein the support surface terminates distal to a patient's calf when the patient's foot is placed within the device, the support surface including a heel aperture sized to permit the heel to sink therein and be suspended without contacting the support surface, wherein the support surface and heel aperture are sized to elevate the ankle and heel an elevation of at least 3 inches above the bottom surface, and wherein (i) termination of the support surface distal to the calf and (ii) elevation of the ankle and heel to at least 3 inches above the bottom surface provide sufficient clearance on a posterior side of the knee for gravity to encourage knee extension; and a base attached to the bottom portion of the main body, the base having a generally flat low-friction bottom surface and a raised perimeter that extends upward from the bottom surface of the base to a height so that at least part of the bottom portion and lateral edges of the main body are placed within the base, wherein the low-friction bottom surface of the base facilitates sliding of the device on a surface, the raised perimeter limits snagging or catching of the base, and the main body supports and stabilizes the foot, while performing leg exercises, wherein the inner side surfaces of the lateral ridges limit medial and/or lateral rotation of the patient's foot when placed on the support surface of the medial depression.

* * * * *